(12) United States Patent
Westerlund et al.

(10) Patent No.: US 9,283,263 B2
(45) Date of Patent: Mar. 15, 2016

(54) COMPOSITIONS AND METHODS FOR ENHANCING RECOVERY AFTER SURGERY OR AN ATHLETIC PERFORMANCE

(71) Applicant: Top Doctors Labs, Fairfield, CA (US)

(72) Inventors: Erik Westerlund, Columbus, GA (US); Martin Wynkoop, Gainesville, FL (US); Robert Brudney, Fairfield, CA (US)

(73) Assignee: Top Doctors Labs, LLC, Fairfield, CA (US)

( * ) Notice: Subject to any disclaimer, the term of this patent is extended or adjusted under 35 U.S.C. 154(b) by 0 days.

(21) Appl. No.: 14/103,498

(22) Filed: Dec. 11, 2013

(65) Prior Publication Data

US 2014/0161784 A1 Jun. 12, 2014

Related U.S. Application Data

(60) Provisional application No. 61/736,187, filed on Dec. 12, 2012.

(51) Int. Cl.

| | |
|---|---|
| *A61K 31/675* | (2006.01) |
| *A61K 38/48* | (2006.01) |
| *A61K 31/07* | (2006.01) |
| *A61K 31/122* | (2006.01) |
| *A61K 31/196* | (2006.01) |
| *A61K 31/197* | (2006.01) |
| *A61K 31/352* | (2006.01) |
| *A61K 31/375* | (2006.01) |
| *A61K 31/4188* | (2006.01) |
| *A61K 31/4415* | (2006.01) |
| *A61K 31/455* | (2006.01) |
| *A61K 31/51* | (2006.01) |
| *A61K 31/519* | (2006.01) |
| *A61K 31/525* | (2006.01) |
| *A61K 31/593* | (2006.01) |
| *A61K 31/714* | (2006.01) |
| *A61K 33/04* | (2006.01) |
| *A61K 33/06* | (2006.01) |
| *A61K 33/18* | (2006.01) |
| *A61K 33/22* | (2006.01) |
| *A61K 33/24* | (2006.01) |
| *A61K 33/30* | (2006.01) |
| *A61K 33/32* | (2006.01) |
| *A61K 33/34* | (2006.01) |
| *A61K 36/185* | (2006.01) |
| *A61K 31/355* | (2006.01) |

(52) U.S. Cl.
CPC ............... *A61K 38/48* (2013.01); *A61K 31/07* (2013.01); *A61K 31/122* (2013.01); *A61K 31/196* (2013.01); *A61K 31/197* (2013.01); *A61K 31/352* (2013.01); *A61K 31/355* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/593* (2013.01); *A61K 31/714* (2013.01); *A61K 33/04* (2013.01); *A61K 33/06* (2013.01); *A61K 33/18* (2013.01); *A61K 33/22* (2013.01); *A61K 33/24* (2013.01); *A61K 33/30* (2013.01); *A61K 33/32* (2013.01); *A61K 33/34* (2013.01); *A61K 36/185* (2013.01); *A61K 38/4873* (2013.01)

(58) Field of Classification Search
IPC ................ A61K 31/675,31/352, 31/355, 31/69, A61K 38/48
See application file for complete search history.

(56) References Cited

U.S. PATENT DOCUMENTS

| | | | |
|---|---|---|---|
| 5,514,382 A | 5/1996 | Sultenfuss | |
| 6,048,846 A | 4/2000 | Cochran | |
| 7,670,612 B2 | 3/2010 | Miller | |
| 8,067,045 B2 | 11/2011 | Smidt et al. | |
| 2004/0253227 A1 | 12/2004 | Martin et al. | |
| 2004/0254095 A1* | 12/2004 | Martin et al. | ..................... 514/2 |
| 2011/0293759 A1 | 12/2011 | Westerlund | |

OTHER PUBLICATIONS

Aprahamian et al., Effects of supplemental pantothenic acid on wound healing: experimental study in rabbit. Am J Clin Nutr. Mar. 1985;41(3):578-89.

(Continued)

*Primary Examiner* — Rosanne Kosson
(74) *Attorney, Agent, or Firm* — Wolf, Greenfield & Sacks, P.C.

(57) ABSTRACT

The invention provides compositions and dosage forms, e.g., in the form of dietary supplements, such as pills, tablets, beverages, or gels, that enhance recovery after surgery or after an athletic performance. An exemplary composition or dosage form comprises about 5000 IU of vitamin A, about 15 mg of vitamin B1, about 34 mg of vitamin B2, about 25 mg of vitamin B3, about 50 mg of vitamin B5, about 20 mg of vitamin B6, about 90 μg of vitamin B12, about 300 mg of vitamin C, about 500 IU of vitamin D, about 60 IU of vitamin E, about 160 μg of vitamin K1, about 5 μg of vitamin K2, about 300 μg of biotin, about 400 μg of folate, about 30 μg of PABA, about 1 mg of boron, about 200 μg of chromium, about 500 μg of copper, about 150 mg of magnesium, about 5 μg of manganese, about 100 μg of molybdenum, about 135 μg of selenium, about 100 μg of vanadium, about 20 mg of zinc, about 150 μg of iodine, about 1.2 mg of pomegranate extract, about 250 mg of bromelain, and about 250 mg of quercetin. Methods for using the compositions and dosage forms for enhancing recovery after surgery or after an athletic performance are also provided herein. The invention also provides kits comprising a composition or dosage form described herein.

19 Claims, No Drawings

(56) References Cited

OTHER PUBLICATIONS

Bal et al., Nutritional deficiencies after bariatric surgery. Nat Rev Endocrinol. Sep. 2012;8(9):544-56. doi:10.1038/nrendo.2012.48. Epub Apr. 24, 2012. Abstract only.

Braga et al., preoperative antioxidants in pancreatic surgery: a double-blind, randomized, clinical trial. Nutrition. Feb. 2012;28(2):160-4. doi: 10.1016/j.nut.2011.05.014. Epub Sep. 3, 2011. Abstract only.

Broughton et al., Use of herbal supplements and vitamins in plastic surgery: a practical review. Plast Reconstr Surg. Mar. 2007;119(3):48e-66e. Abstract only.

Donadelli et al., Daily vitamin supplementation and hypovitaminosis after obesity surgery. Nutrition. Apr. 2012;28(4):391-6. doi: 10.1016/j.nut.2011.07.012. Epub Nov. 4, 2011. Abstract only.

Fukushima et al., Vitamin C requirement in surgical patients. Curr Opin lin Nutr Metab Care. Nov. 2010;13(6):669-76. doi: 10.1097/MCO.0b013e32833e05bc. Abstract only.

Jurenka, Therapeutic applications of pomegranate (*Punica granatum* L.): a review. Altern Med Rev. Jun. 2008;13(2):128-44.

Lizer et al., Nutritional and pharmacologic challenges in the bariatric surgery patient. Obes Surg. Dec. 2010;20(12):1654-9. doi:10.1007/s11695-009-0050-1. Epub Jan. 27, 2010. Abstract only.

Malone, Recommended nutritional supplements for bariatric surgery patients. Ann Pharmacother. Dec. 2008;42(12):1851-8. doi: 10.1345/aph.1L321. Epub Nov. 18, 2008. Abstract only.

Matrana et al., Vitamin deficiency after gastric bypass surgery: a review. South Med J. Oct. 2009;102(10):1025-31. doi: 10.1097/SMJ.0b013e3181b62614. Abstract only.

O'Dell, Role of zinc in plasma membrane function. J Nutr. May 2000;130(5S Suppl):1432S-6S.

Poggioli et al., Nutritional status and behavior in subjects with type 1 diabetes, before and after islet transplantation. Transplantation. Feb. 27, 2008;85(4):501-6. doi: 10.1097/TP.0b013e3181629d7b. Abstract only.

Rickers et al., Bariatric surgery: nutritional considerations for patients. Nurs Stand. Aug. 8-14, 2012;26(49):41-8. Abstract only.

Rudnicki, Prevention and treatment of peripheral neuropathy after bariatric surgery. Curr Treat Options Neurol. Jan. 2010;12(1):29-36. doi:10.1007/s11940-009-0052-2. Abstract only.

Segaert, Vitamin D regulation of cathelicidin in the skin: toward a renaissance of vitamin D in dermatology? J Invest Dermatol. Apr. 2008;128(4):773-5. doi: 10.1038/jid.2008.35.

Shankar et al., Micronutrient deficiencies after bariatric surgery. Nutrition. Nov.-Dec. 2010;26(11-12):1031-7. doi:10.1016/j.nut.2009.12.003. Epub Apr. 3, 2010. Abstract only.

Uauy et al., Essentiality of copper in humans. Am J Clin Nutr. May 1998;67(5 Suppl):952S-959S.

Vargas-Ruiz et al., Prevalence of iron, folate, and vitamin B12 deficiency anemia after laparoscopic Roux-en-Y gastric bypass. Obes Surg. Mar. 2008;18(3):288-93. doi: 10.1007/s11695-007-9310-0. Epub Jan. 23, 2008. Abstract only.

Watters et al., Limited effects of micronutrient supplementation on strength and physical function after abdominal aortic aneurysmectomy. Clin Nutr. Aug. 2002;21(4):321-7. Abstract only.

Weimann et al., Studies on wound healing: effects of calcium D-pantothenate on the migration, proliferation and protein synthesis of human dermal fibroblasts in culture. Int J Vitam Nutr Res. Mar. 1999;69(2):113-9. Abstract only.

* cited by examiner

COMPOSITIONS AND METHODS FOR ENHANCING RECOVERY AFTER SURGERY OR AN ATHLETIC PERFORMANCE

RELATED APPLICATIONS

This application claims priority under 35 U.S.C. §119(e) to U.S. provisional patent application, U.S. Ser. No. 61/736,187, filed Dec. 12, 2012, which is incorporated herein by reference.

BACKGROUND OF THE INVENTION

Surgery and athletic performance cause an increased need for micronutrients, for example, vitamins, minerals, and antioxidants in the human body. There is a need for dietary supplements containing effective doses of such micronutrients for providing nutritional support during and after surgery or an athletic performance.

SUMMARY OF THE INVENTION

The present disclosure is based on the finding that certain micronutrients, for example, vitamins, minerals, and co-factors, such as enzymes (e.g., proteases), flavonoids, and antioxidants, support recovery from surgery or an athletic performance. In one aspect, this disclosure provides compositions, for example, dietary supplements, comprising micronutrients. Dosage forms of such compositions, kits, and methods of using such compositions are also provided herein.

In one aspect, this disclosure provides a composition, e.g., a dietary supplement (such as, e.g., a pill, tablet, beverage, solution, tincture, syrup, powdered drink, or effervescent tablet, comprising (a) one or more vitamins, wherein the one or more vitamins is selected from the group consisting of B vitamins and vitamin E; (b) a mineral, wherein the mineral comprises boron; and (c) one or more co-factors, wherein the one or more co-factors is selected from the group consisting of proteases and flavonoids. In some embodiments, the B vitamin is selected from the group consisting of vitamin B1, vitamin B2, vitamin B3, vitamin B5, vitamin B6, and vitamin B12. In some embodiments, the vitamin B1 comprises thiamine, the Vitamin B2 comprises riboflavin, the Vitamin B3 comprises niacin, the Vitamin B5 comprises pantothenic acid and/or pantothenate, the Vitamin B6 comprises pyridoxine and/or pyridoxal, and/or the Vitamin B12 comprises cobalamin. In some embodiments, the composition further comprises a vitamin selected from the group consisting of vitamin A, vitamin C, vitamin D, vitamin K, biotin, folic acid, para-aminobenzoic acid (PABA), and pharmaceutically acceptable salts thereof. In some embodiments, the vitamin D is Vitamin D3. In some embodiments, the vitamin K is vitamin K1 and/or vitamin K2. In some embodiments, the vitamin A is beta-carotene, retinol, and/or retinoic acid; the vitamin C is ascorbic acid and/or a salt thereof; the vitamin D is cholecalciferol; the vitamin E is tocopherol, and/or the vitamin K is phylloquinone and/or menatetranone. In some embodiments, the composition further comprises one or more additional minerals selected from the group consisting of chromium, copper, magnesium, manganese, molybdenum, selenium, vanadium, zinc, iodine, and calcium. In some embodiments, the mineral is provided as a pharmaceutically acceptable salt, for example, a salt with a counterion selected from the group consisting of acetate, ascorbate, citrate, malate, succinate, picolinate, and methionine (also referred to sometimes as methianone), or any pharmaceutically acceptable salt described herein. In certain embodiments, the protease is a plant protease. In some embodiments, the protease is bromelain. In some embodiments, the flavonoid is quercetin. In certain embodiments, the composition comprises vitamin A, vitamin B1, vitamin B2, vitamin B3, vitamin B5, vitamin B6, vitamin B12, vitamin C, vitamin D, vitamin E, vitamin K, biotin, folate, PABA, boron, chromium, copper, magnesium, manganese, molybdenum, selenium, vanadium, zinc, iodine, bromelain, and a flavonoid. In some embodiments, the flavonoid is quercetin. In some embodiments, the composition further comprises an antioxidant. In some embodiments, the antioxidant is a plant extract. In some embodiments, the antioxidant is pomegranate extract. In some embodiments, the composition further comprises calcium. In certain embodiments, the composition consists essentially of vitamin A, vitamin B1, vitamin B2, vitamin B3, vitamin B5, vitamin B6, vitamin B12, vitamin C, vitamin D, vitamin E, vitamin K, biotin, folate, PABA, boron, chromium, copper, magnesium, manganese, molybdenum, selenium, vanadium, zinc, iodine, bromelain, and a flavonoid. In certain embodiments, the composition consists essentially of vitamin A, vitamin B1, vitamin B2, vitamin B3, vitamin B5, vitamin B6, vitamin B12, vitamin C, vitamin D, vitamin E, vitamin K, biotin, folate, PABA, boron, chromium, copper, magnesium, manganese, molybdenum, selenium, vanadium, zinc, iodine, bromelain, a flavonoid, and an antioxidant. In certain embodiments, the composition consists essentially of vitamin A, vitamin B1, vitamin B2, vitamin B3, vitamin B5, vitamin B6, vitamin B12, vitamin C, vitamin D, vitamin E, vitamin K, biotin, folate, PABA, boron, chromium, copper, magnesium, manganese, molybdenum, selenium, vanadium, zinc, iodine, bromelain, a flavonoid, an antioxidant, and calcium. In certain embodiments, the composition consists of vitamin A, vitamin B1, vitamin B2, vitamin B3, vitamin B5, vitamin B6, vitamin B12, vitamin C, vitamin D, vitamin E, vitamin K, biotin, folate, PABA, boron, chromium, copper, magnesium, manganese, molybdenum, selenium, vanadium, zinc, iodine, bromelain, a flavonoid, and an antioxidant. In certain embodiments, the composition consists of vitamin A, vitamin B1, vitamin B2, vitamin B3, vitamin B5, vitamin B6, vitamin B12, vitamin C, vitamin D, vitamin E, vitamin K, biotin, folate, PABA, boron, chromium, copper, magnesium, manganese, molybdenum, selenium, vanadium, zinc, iodine, bromelain, a flavonoid, an antioxidant, and calcium.

In some embodiments, components of the composition, e.g., a vitamin, a mineral, a protease, and/or a flavonoid, are present in a therapeutically or prophylactically effective amount. The amounts provided herein typically refer to the form of the respective component used in the composition, e.g., the salt or derivative of the vitamin or mineral used, not of the zero-valent form. For example, a composition comprising boron in an amount of about 250 µg to about 2.5 mg refers to a composition comprising about 250 µg to about 2.5 mg of the respective form of boron used in the composition, typically a salt of boron, such as boron ascorbate, and not to the amount of zero-valent boron within the composition. In some embodiments, vitamin A is present in the composition in an amount of about 1000 IU to about 1000 IU, or of about 50% to about 150% RID. In some embodiments, the vitamin A comprises about 15% retinoic acid, or a salt thereof, and about 85% beta-carotene. In some embodiments, vitamin B1 is present in an amount of about 1 mg to about 50 mg, or of about 250% to about 2500% RID. In some embodiments, vitamin B2 is present in an amount of about 1 mg to about 50 mg, or of about 500% to about 5000% RID. In some embodiments, the vitamin B2 comprises about 90% riboflavin and about 10% riboflavin 5'-monophosphate. In some embodiments, vitamin B3 is present in an amount of about 1 mg to about 50 mg, or of about 30% to about 300% RID. In some embodiments, vitamin B5 is present in an amount of about 5 mg to about 200 mg, or of about 125% to about 1250% RID. In some embodiments, vitamin B6 is present in an amount of about 1 mg to about 50 mg, or of about 250% to about 2500% RID. In some embodiments, the vitamin B6 comprises about 80% pyridoxine and about 20% pyridoxal 5'-phosphate. In some embodiments, vitamin B12 is present in an amount of about 25 µg to about 250 µg, or of about 400% to about 4000% RID. In some embodiments, vitamin C is present in an amount of about 75 mg to about 750 mg, or of about 125% to about 1250% RID. In some embodiments, vitamin D is present in an amount of about 125 IU to about 1250 IU, or of about 50% to about 500% RID. In some embodiments, vitamin E is present in an amount of about 20 IU to about 200 IU, or of about 50% to about 500% RID. In some embodiments, vitamin K is present in an amount of about 50 µg to about 500 µg, or of about 50% to about 500% RID. In some embodiments, the vitamin K comprises about 97% vitamin K1 and about 3% vitamin K2. In some embodiments, biotin is present in an amount of about 75 µg to about 750 µg, or of about 25% to about 250% RID. In some embodiments, folate is present in an amount of about 100 µg to about 400 µg, or of about 25% to about 250% RID. In some embodiments, PABA is present in an amount of about 7.5 µg to about 75 µg. In some embodiments, boron is present in an amount of about 250 µg to about 2.5 mg. In some embodiments, chromium is present in an amount of about 50 µg to about 500 µg, or of about 50% to about 500% RID. In some embodiments, the chromium is in a form comprising about 50% chromium picolinate and about 50% chromium ascorbate. In some embodiments, copper is present in an amount of about 125 µg to about 500 µg, or of about 5% to about 75% RID. In some embodiments, magnesium is present in an amount of about 40 mg to about 400 mg, or of about 10% to about 100% RID. In some embodiments, the magnesium is provided in a form selected from the group consisting of magnesium citrate, magnesium malate, and magnesium succinate. In some embodiments, manganese is present in an amount of about 1 µg to about 10 µg, or of about 50% to about 750% RID. In some embodiments, molybdenum is present in an amount of about 25 µg to about 250 µg, or of about 30% to about 500% RID. In some embodiments, selenium is present in an amount of about 30 µg to about 300 µg, or of about 40% to about 400% RID. In some embodiments, vanadium is present in an amount of about 25 µg to about 250 µg. In some embodiments, zinc is present in an amount of about 5 mg to about 50 mg, or of about 30% to about 300% RID. In some embodiments, iodine is present in an amount of about 40 µg to about 400 µg, or of about 25% to about 250% RID. In some embodiments, bromelain is present in an amount of about 50 mg to 750 mg. In some embodiments, a flavonoid is present in an amount of about 50 mg to 750 mg. In some embodiments, quercetin is present in an amount of about 50 mg to 750 mg. In some embodiments, the pomegranate extract is present in an amount of about 0.3 mg to about 3 mg.

In some embodiments, the compositions provided herein comprise a micronutrient in an amount of equal to or less than a "tolerable upper intake level," also sometimes referred to as the "UL," or of less than an amount deemed to be toxic. Tolerable upper intake levels and toxic levels of the nutrients described herein are dependent on the age, sex, weight, and health of the subject to which they are administered, and such levels are known to those of skill in the art. Typically such levels are provided by established dietary intake guidelines or toxicity guidelines. Non-limiting examples of such guidelines providing tolerable upper intake levels and/or toxicity levels include, without limitation, guidelines published by the Institute of Medicine of the National Academies, the U.S. Food and Nutrition Board, and the European Food Safety Authority. See, e.g., EFSA—European Food Safety Authority, *Tolerable Upper Intake Levels for Vitamins and Minerals*, Dictus Publishing (Mar. 30, 2011), ISBN-10: 3843332053; the entire contents of which are incorporated by reference herein. In some embodiments, the tolerable upper intake level of a nutrient described herein is the UL amount provided in Table 1.

In some embodiments, the composition comprises about 5000 IU of vitamin A, about 15 mg of vitamin B1, about 34 mg of vitamin B2, about 25 mg of vitamin B3, about 50 mg of vitamin B5, about 20 mg of vitamin B6, about 90 µg of vitamin B12, about 300 mg of vitamin C, about 500 IU of vitamin D, about 60 IU of vitamin E, about 160 µg of vitamin K1, about 5 µg of vitamin K2, about 300 µg of biotin, about 400 µg of folate, about 30 µg of PABA, about 1 mg of boron, about 200 µg of chromium, about 500 µg of copper, about 150 mg of magnesium, about 5 µg of manganese, about 100 µg of molybdenum, about 135 µg of selenium, about 100 µg of vanadium, about 20 mg of zinc, about 150 µg of iodine, about 1.2 mg of pomegranate extract, about 250 mg of bromelain, and about 250 mg of quercetin.

In another aspect, this disclosure provides dosage forms of a composition described herein. In some embodiments, the dosage form is formulated for oral administration. In some embodiments, the dosage form further comprises a pharmaceutically acceptable carrier or excipient. In some embodiments, the carrier comprises a vegetable fiber matrix. The term dosage form, as used herein, refers to a formulation of a composition as described herein for administration to a subject. Typically, a dosage form comprises a mixture of active components, e.g., of vitamins, minerals, and co-factors as described herein, and inactive components, e.g., of pharmaceutically acceptable carriers and/or excipients. In some embodiments, the dosage form is a liquid dosage form, a solid dosage form, or a semi-solid dosage form. In some embodiments, the dosage form is a form of dietary supplement, for example, a dosage form for oral administration. In some embodiments, a dosage form is a pill, tablet, or capsule; e.g., a specialty tablet, such as a buccal, sub-lingual, or orally-disintegrating tablet, or an effervescent tablet; a gel; a thin film; a liquid solution or suspension (e.g., a beverage, drink, tincture, or syrup); a powder or solid crystals; or a paste.

In another aspect, this disclosure provides methods of administering an inventive composition or dosage form to a subject (e.g., human). The methods comprise administering an effective amount of a composition described herein, or a dosage form described herein, to a subject. In some embodiments, the administration is in temporal proximity to the subject undergoing a surgery. In some embodiments, the administration is peri-operative or post-operative. In certain embodiments, the surgery is cardiac surgery, urology surgery, gynecologic surgery, ocular surgery, plastic surgery, bariatric surgery, shoulder surgery, elbow surgery, hand surgery, hip surgery, knee surgery, ankle surgery, spine surgery, orthopedic surgery, or brain surgery. In some embodiments, the administration is in temporal proximity to an athletic performance (e.g., marathon, triathlon) by the subject. In some embodiments, the composition or dosage form is administered orally. In some embodiments, the step of administering is repeated. In certain embodiments, the step of administering is repeated over a time period of at least 1 week, at least 2 weeks, at least 3 weeks, at least 4 weeks, at least 2 months, at least 3 months, at least 4 months, at least 5 months, at least 6 months, at least 8 months, at least 10 months, or at least 1 year.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

DETAILED DESCRIPTION OF CERTAIN EMBODIMENTS OF THE INVENTION

The present invention is based on the finding that compositions of vitamins, minerals, and other nutrients, as described herein enhance recovery from surgery and athletic performance.

The term vitamin, as used herein, refers to an organic compound that is essential as a vital nutrient for a subject, and is not synthesized in sufficient quantities by the subject. Exemplary vitamins include, without limitation, vitamin A, vitamin B (e.g., vitamin B1, vitamin B2, vitamin B3, vitamin B5, vitamin B6, vitamin B12), vitamin C, vitamin D (e.g., vitamin D3), vitamin E, vitamin K (e.g., vitamin K1, vitamin K2), biotin, folate, folic acid, lipoic acid, ascorbic acid, choline, carnitine, carotene (e.g., beta carotene, alpha carotene, gamma carotene), and salts and derivatives thereof. Also included within the term vitamin are derivatives of vitamins and molecules that are associated with or products of the synthesis, absorption, or processing of a vitamin, e.g., thiamine pyrophosphates (TPP), flavin mononucleotides (FMM), flavin adenine dinucleotides (FAD), nicotinamide adenine dinucleotides (NAD), nicotinamide adenine dinucleotide phosphate (NADP), coenzyme-A (CoA) pyridoxal phosphate, biocytin, tetrahydrofolic acid, coenzyme B12, lipoyllysine, 1,1-cis-retinal, and 1,2,5-dihydroxycholecalciferol.

The term effective amount, as used herein with a component of a composition described herein, e.g., a vitamin, a mineral, a co-factor, or other nutrient, refers to an amount that can induce a desired effect in a subject. In general, an effective amount is an amount that can cause a beneficial change in a subject, e.g., an enhancement of recovery from surgery or an athletic performance, such as, for example, a recovery in less time than the average time for recovery among a group of subjects, or a recovery to a higher level of functionality or performance than the average recovered level of functionality or performance. In general, an effective amount is that amount of a pharmaceutical preparation that alone, or together with further doses, produces a desired response. An effective amount of a vitamin is, in some embodiments, at least 10%, at least 15%, at least 20%, or at least 25% of the United States Recommended Daily Allowance (RDA) or the recommended daily intake (RDI) for a subject. In some embodiments, an effective amount in the context of compositions provided herein are higher, however, for example, at least 30%, at least 40%, at least 50%, at least 60%, at least 70%, at least 80%, at least 90%, or at least 100%. In some embodiments, an effective amount of a compound provided herein, e.g., a vitamin, mineral, or co-factor, is in excess of 100% RDA or RDI, e.g., at least 150%, at least 200%, at least 250%, at least 300%, at least 400%, at least 500%, at least 600%, at least 700%, at least 800%, at least 900%, at least 1000%, at least 2000%, at least 2500%, at least 3000%, at least 4000%, or at least 5000%. In some embodiments, the effective amount is higher than 5000% RDI or RDA. In some embodiments, RDA and RDI values provided by official government agencies, such as the U.S. Food and Drug Administration (FDA), are used to compute effective amounts. Some exemplary RDI values for some of the vitamins and minerals in the compositions described herein are listed in Table 1.

However, additional suitable values for RDA and RDI, e.g., released from different agencies, will be apparent to those of skill in the art and the disclosure is not limited in this respect. It will also be understood that the effective amount of each component of the compositions described herein may be less than 10% of the RDI or RDA, or may exceed 100% of the RDI or RDA. The compositions provided herein may further include components, e.g., vitamins, minerals, or co-factors, for which no RDI or RDA has been determined, e.g., by the U.S. FDA.

TABLE 1

Exemplary nutrient RDI and UL values.

| Nutrient | RDI | UL |
|---|---|---|
| Vitamin A (e.g., beta carotene) | 900 µg (5000 IU) | 3000 µg |
| VitaminB1 (e.g., thiamine) | 1.5 mg | ND |
| Vitamin B2 (e.g., riboflavin) | 17 mg | ND |
| Vitamin B3 (e.g., niacin) | 20 mg | 35 mg |
| Vitamin B5 (e.g., pantothenate) | 10 mg | ND |
| Vitamin B6 (e.g., pyridoxine) | 2 mg | 100 mg |
| Vitamin B12 (e.g., cobalamin) | 60 µg | ND |
| Vitamin C (e.g., ascorbate) | 60 mg | 2000 mg |
| Vitamin D3 (e.g., cholecalciferol) | 400 IU | 2,000 IU |
| Vitamin E (e.g., tocopherol) | 30 IU | 1000 mg (~1100-1500 IU) |
| Vitamin K1 (e.g., phylloquinone) | 80 µg | ND |
| Biotin | 300 µg | ND |
| Folate | 400 µg | 1000 µg |
| Calcium (e.g., calcium citrate) | 1000 mg | 2500 mg |
| Chromium (e.g., chromium ascorbate) | 120 µg | ND |
| Copper (e.g., copper citrate) | 2 mg | 10 mg |
| Iodine | 150 µg | 1100 µg |
| Magnesium (e.g., magnesium citrate) | 400 mg* | 350 mg** |
| Manganese (e.g., manganese ascorbate) | 2 mg | 11 mg |
| Molybdenum (e.g., molybdenum ascorbate) | 75 µg | 2000 µg |
| Selenium (e.g., L-selenomethianone) | 90 µg | 400 µg |
| Zinc (e.g., Zinc ascorbate) | 15 mg | 40 mg |

RDI: recommended daily intake. UL: tolerable upper intake level. ND: not determined.
*total intake from food and dietary supplements.
**total intake from supplements.

The term mineral, as used herein, refers to a dietary mineral, and includes, for example, a chemical element required by a living organism to be present in the organism's diet. Non-limiting examples of minerals include calcium, phosphorus, potassium, sulfur, sodium, iron, zinc, selenium, copper, cobalt, iodine, magnesium, manganese, chromium, molybdenum, chlorine, sodium, potassium, nickel, silicon, boron, vanadium, silicon, and derivatives, salts, chelates, and other compositional forms and combinations thereof.

An effective amount of a mineral contained in a composition or dosage form provided herein is generally at least 10% of the U.S. FDA-recommended RDI or RDA for a subject. For example, an effective amount of calcium may, in some embodiments, include an amount of calcium sufficient to provide 10% or more of the RDI or RDA. However, it should be understood that the amount of each mineral component in a composition or dosage form provided herein may be less than 10% of the RDI or RDA, may exceed 100% of the RDI or RDA, or the mineral may be present regardless of whether an RDI or RDA has been determined or released.

The term co-factor, as used herein, refers to a beneficial, non-essential nutrient. Some examples of co-factors include, without limitation, proteases, e.g., bromelain and papain, flavonoids, e.g., quercetin, quercitrin, rutin, and epicatechin. Additional co-factors include, without limitation, plant extracts, for example, plant extracts having antioxidant properties, e.g., pomegranate extract.

The term protease, as used herein, refers to an enzyme that catalyzes a proteolytic reaction, for example, by hydrolyzing peptide bonds between amino acid residues of a protein or peptide.

The term flavonoid, as used herein, refers to a compound of a class of secondary plant metabolites that includes flavones, isoflavonoids, neoflavonoids, anthocyanidins, and flavanols. Non-limiting examples of flavonoids, which are also sometimes referred to as bioflavonoids, are quercetin, rutin, kaempferol, astragalin, naringenin, sophoroflavonoloside, hesperidin, taxifolin, dihydroquercetin, dihydrokaempferol, genistein, daidzein, glycitein, equol, lonchocarpane, laxiflorane, calophyllolide, dalbergichromene, coutareagenin, dalbergin, and nivetin.

The term antioxidant, as used herein, refers to a substance that inhibits oxidation. In some embodiments, an antioxidant is a scavenger of free reactive oxygen species. Some of the vitamins (e.g., beta-carotene, vitamin C) and some other compounds listed herein, e.g., some flavonoids, have antioxidant properties. The term antioxidant also includes, without limitation, lutein, zeaxanthin, astaxanthin lycopene, and various extracts of plants and fruits, such as pomegranate extract, glutathione, thioredoxin, lipoic acid, uric acid, tocopherol, ubiquinol, resveratrol, and carotenoids.

Some aspects of this disclosure provide compositions comprising nutrients that have been found to be beneficial for recovery from surgery or an athletic performance. In some embodiments, compositions and dosage forms are provided in the form of a dietary supplement, e.g., in a tablet or powder form. Some aspects of this invention provide a composition that comprises one or more vitamins and one or more minerals as well as one or more co-factors. In some embodiments, the composition is for daily use, e.g., for daily oral administration to a subject, to support recovery of the subject after surgery or recovery of the subject after an athletic performance. In some embodiments, the composition is formulated to support tissue recovery and regeneration, and to help decrease recovery time.

In some embodiments, a composition is provided herein that is formulated to enhance recovery after surgery or an athletic performance, using a formulation strategy that is targeted specifically to meet the demands of the post-operative subject, and using dosage levels and compounds, e.g., vitamins, minerals, and co-factors, that, in combination, enhance recovery. In some embodiments, the compositions and dosage forms are formulated to permit long-term daily use. Such compositions and dosage forms are, accordingly suitable for administration to subjects facing a long period of recovery, e.g., after major surgical interventions.

In general, the compositions described herein include compounds that promote post-operative healing, and that are also capable of meeting tissue and cellular recovery demands of a subject during periods of intense athletic training and competition. In some embodiments, the components of the compositions provided herein comprise combinations of vitamins, minerals, and co-factors that are optimized to meet the needs of the recovering body in order to generate an optimal tissue recovery response. In general, the compositions provided herein comprise components that are regarded as safe peri-operatively and post-operatively, and are selected to comply with recommendations from the American Association of Anesthesiologists and others. For example, in some embodiments, the compositions provided herein contain optimized levels of vitamin B, vitamin E, boron, and co-factors, such as bromelain and quercetin.

In general, the compositions provided herein comprise a vitamin, a mineral, and a co-factor. In some embodiments, the vitamin portion of the composition comprises vitamin B and vitamin E. In some embodiments, the mineral is boron. In some embodiments, the co-factor is a protease and/or a flavonoid, such as, for example, bromelain and quercetin, respectively. In some embodiments, the B vitamin is a vitamin of the B vitamin complex, e.g., vitamin B1, vitamin B2, vitamin B3, vitamin B5, vitamin B6, and vitamin B12. In some embodiments, a component, some components, or all components of a composition provided herein are in the form of a pharmaceutically acceptable salt.

In some embodiments, the vitamin B1 comprises thiamine, the vitamin B2 comprises riboflavin, the vitamin B3 comprises niacin, the vitamin B5 comprises pantothenic acid and/or pantothenate, the vitamin B6 comprises pyridoxine and/or pyridoxal, and/or the vitamin B12 comprises cobalamin. However, other forms, salts, derivatives, and solvates of any of the B vitamins that are known to those of skill in the art may also be used in the compositions provided herein.

In some embodiments, the composition further comprises one or more additional vitamins selected from the group consisting of vitamin A, vitamin C, vitamin D, vitamin K, biotin, folic acid, folate, para-aminobenzoic acid (PABA), and salts thereof.

Without wishing to be bound by any particular theory, the B vitamin complex members play important roles in tissue healing, recovery, and homeostasis, and some of the B complex members accelerate wound healing and increase the strength and integrity of healing tissues. Vitamin E is a potent antioxidant and supports cell-cell-signaling in healing tissue. It also enhances neurological functions. In some embodiments, Vitamin E is provided at a low dose or very low dose (VLD), e.g., a dose equal to or less than 60 IU, less than 50 IU, less than 40 IU, less than 30 IU, less than 20 IU, less than 10 IU, less than 5 IU, less than 2.5 IU, less than 2 IU, less than 1 IU, less than 0.5 IU, or less than 0.1 IU of Vitamin E, which results in the provision of optimized trace vitamin E support in forms and amounts ideal to meet biologic needs while minimizing the potential for adverse peri-surgical effects, such as increased bleeding. Vitamin A, commonly known as the anti-infective vitamin, supports peri-operative immune function, tissue growth, and recovery, as well as red blood cell production. Vitamin C is a highly effective antioxidant and also essential for the synthesis of collagen in healing blood vessels, bone, tendon, ligaments, and other tissues. Vitamin D plays an important role in cell differentiation in healing skin, bone, and other tissues, and is also important for ideal calcium balance and immune function. Vitamin D also supports healing bone fractures. Vitamin K1 and vitamin K2 are critical elements to foster optimal cell growth, blood clotting (to minimize bleeding potential), and support bone mineralization where needed.

Boron is an important trace mineral that enhances the positive effects of some vitamins, e.g., vitamin D, and supports retention of calcium in the body, which enhances bone formation and healing.

Copper is a co-factor of many enzymes, e.g., cuproenzymes, that are activated in wound healing, and also plays a role in nervous system function. In addition, copper is required for optimized lysyl oxidase support of bone formation. It also acts to support antioxidant activity and is a free-radical scavenger.

Chromium enhances the action of insulin, and thus aids in regulating blood glucose levels. It also plays important roles in metabolizing fats and carbohydrates.

Magnesium supports normal muscle and nerve function, keeps heart rhythm steady, supports a healthy immune system and bone health. Magnesium also helps regulate blood sugar levels, promotes normal blood pressure, and is known to be involved in energy metabolism and protein synthesis.

Manganese plays a role in wound healing, for example through its influence on collagen formation. Manganese is required for the activation of prolidase, an enzyme that functions to provide the amino acid proline for collagen formation in human skin cells. Glycosaminoglycan synthesis also plays and important role in wound healing and requires manganese-activated glycosyltransferases.

Molybdenum is an essential cofactor for many of the enzymes, including sulfite oxidase, which plays an important role in the metabolism of amino acids that contain sulfur, such as methionine and cysteine, aldehyde oxidase, which metabolizes some important toxins, and xanthine oxidase, which breaks down nucleotides, which are precursors to RNA and DNA, to produce uric acid, a plasma antioxidant.

Selenium is comprised in selenoproteins, which are important antioxidant enzymes. The antioxidant properties of selenoproteins help prevent cellular damage from free radicals. Some selenoproteins also help regulate thyroid function and support immune system function.

Vanadium enhances insulin action and normalizes blood glucose levels. It also plays an important role in tissue homeostasis and bone strength.

Iodine is an essential component of the thyroid hormones thyroxine (T4) and triiodothyronine (T3). Thyroid hormones regulate many important biochemical reactions, including protein synthesis and enzymatic activity, and are critical determinants of metabolic activity. They also support skeletal and central nervous system development and recovery.

Zinc protects cell membranes from oxidative damage and plays an important role in cellular growth and the immune response during healing processes. Calcium, which is included in some embodiments of the compositions provided herein, e.g., as calcium citrate, is critical for healing given its role in bone health, cell signaling, as a cofactor for enzymes and proteins, and nerve and muscle function.

In some embodiments, the composition comprises co-factors that have beneficial effects post-surgery or post-performance recovery, for example, anti-oxidant plant extracts, such as pomegranate extract, proteases such as papain or bromelain, which can reduce inflammatory responses, and flavonoids, such as quercetin, which support and boost the effects of some of the other ingredients of the compositions described herein.

Some compositions provided herein comprise vitamin D, for example, in the form of vitamin D3 (cholecalciferol). Some compositions provided herein comprise vitamin K, e.g., vitamin K1 in the form of phylloquinone and/or vitamin K2 in the form of menatetranone, MK-4, or MK-6. Some compositions provided herein comprise vitamin A, e.g., in the form of beta-carotene, retinol, and/or retinoic acid. Some compositions provided herein comprise vitamin C in the form of ascorbic acid and/or ascorbate. Some compositions provided herein comprise vitamin E in the form of tocopherol. Other suitable forms, including derivatives, solvates, and salts of the vitamins described herein, will be apparent to those of skill in the art, and the disclosure is not limited in this respect.

In some embodiments, the mineral in the composition comprises a mineral selected from the group consisting of, chromium, copper, magnesium, manganese, molybdenum, selenium, vanadium, zinc, iodine, and calcium. In some embodiments, at least one mineral is provided as a pharmaceutically acceptable salt. In some embodiments, at least one mineral is provided as a salt selected from the group consisting of acetate, ascorbate, citrate, malate, succinate, picolinate, and methionine. For example, in some embodiments, boron is present as boron ascorbate, chromium is present as chromium picolinate and/or chromium ascorbate, copper is present as copper citrate, magnesium is present as magnesium citrate, magnesium malate, and/or magnesium succinate, manganese is present as manganese ascorbate, molybdenum is present as molybdenum ascorbate, potassium is present as potassium citrate, selenium is present as L-selenomethianone, vanadium is present as vanadium ascorbate, and zinc is present as zinc picolinate. In another embodiment, the calcium present in a composition provided herein is not in the form of calcium carbonate or calcium citrate.

The term pharmaceutically acceptable salt, as used herein, e.g., in the context of components comprised in compositions for administration to a subject, refers to those salts which are, within the scope of sound medical judgment, suitable for use in contact with the tissues of humans and lower animals without undue toxicity, irritation, immunological response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds, e.g., of vitamins and/or minerals described herein, include, for example, those derived from suitable inorganic and organic acids and bases. Non-limiting examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid, a salt formed by a naturally occurring amino acid, or formed by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picolinate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include non-toxic ammonium, quaternary ammonium, and amine cations formed using counterions such as halide, hydroxide, carboxylate, sulfate, phosphate, nitrate, lower alkyl sulfonate, and aryl sulfonate.

In some embodiments, the protease is a plant protease. In some embodiments, the protease comprises bromelain (e.g., from pineapple), papain (e.g., from papaya), actinidin (e.g., from kiwi fruit), or ficin (e.g., from figs). The protease may be provided as a purified or partially purified protease or as part of a plant extract. In some embodiments, the flavonoid comprises quercetin or rutin.

One exemplary composition provided herein comprises vitamin A, vitamin B1, vitamin B2, vitamin B3, vitamin B5, vitamin B6, vitamin B12, vitamin C, vitamin D, vitamin E, vitamin K, biotin, folate, PABA, boron, chromium, copper, magnesium, manganese, molybdenum, selenium, vanadium, zinc, iodine, bromelain, and a flavonoid. In some embodiments, the flavonoid comprises quercetin. In some embodiments, the composition further comprises an antioxidant, for example, in the form of a fruit extract such as pomegranate extract. In some embodiments, the composition further comprises calcium. In certain embodiments, the composition consists essentially of vitamin A, vitamin B1, vitamin B2, vitamin B3, vitamin B5, vitamin B6, vitamin B12, vitamin C, vitamin D, vitamin E, vitamin K, biotin, folate, PABA, boron, chromium, copper, magnesium, manganese, molybdenum, selenium, vanadium, zinc, iodine, bromelain, and a flavonoid. In certain embodiments, the composition consists essentially of vitamin A, vitamin B1, vitamin B2, vitamin B3, vitamin B5, vitamin B6, vitamin B12, vitamin C, vitamin D, vitamin E, vitamin K, biotin, folate, PABA, boron, chromium, copper, magnesium, manganese, molybdenum, selenium, vanadium, zinc, iodine, bromelain, a flavonoid, and an antioxidant. In certain embodiments, the composition consists essentially of vitamin A, vitamin B1, vitamin B2, vitamin B3, vitamin B5, vitamin B6, vitamin B12, vitamin C, vitamin D, vitamin E, vitamin K, biotin, folate, PABA, boron, chromium, copper, magnesium, manganese, molybdenum, selenium, vanadium, zinc, iodine, bromelain, a flavonoid, an antioxidant, and calcium. In certain embodiments, the composition consists of vitamin A, vitamin B1, vitamin B2, vitamin B3, vitamin B5, vitamin B6, vitamin B12, vitamin C, vitamin D, vitamin E, vitamin K, biotin, folate, PABA, boron, chromium, copper, magnesium, manganese, molybdenum, selenium, vanadium, zinc, iodine, bromelain, a flavonoid, and an antioxidant. In certain embodiments, the composition consists of vitamin A, vitamin B1, vitamin B2, vitamin B3, vitamin B5, vitamin B6, vitamin B12, vitamin C, vitamin D, vitamin E, vitamin K, biotin, folate, PABA, boron, chromium, copper, magnesium, manganese, molybdenum, selenium, vanadium, zinc, iodine, bromelain, a flavonoid, an antioxidant, and calcium.

Typically, the components of the compositions provided herein, e.g., the vitamin, the mineral, the protease and/or the flavonoid, are present in a therapeutically effective amount. Therapeutically effective amounts of some of the components of the compositions provided herein are known to those of skill in the art, or can be established with no more than routine experimentation.

In some embodiments, vitamin A is present in an amount of about 1000 IU to about 10000 IU, or of about 50% to about 150% RID. In some embodiments, vitamin A is present in an amount of about 1000 IU to about 5000 IU, of about 2500 IU to about 7500 IU, of about 4000 IU to about 6000 IU, or of about 4500 IU to about 5500 IU. In some embodiments, vitamin A is present in an amount of about 1000 IU, about 2000 IU, about 2500 IU, about 3000 IU, about 4000 IU, about 5000 IU, about 6000 IU, about 7000 IU, about 8000 IU, about 9000 IU, or of about 10000 IU. In some embodiments, the Vitamin A comprises about 15% retinoic acid, or a salt thereof, and about 85% beta-carotene.

In some embodiments, vitamin B1 is present in an amount of about 1 mg to about 50 mg, or of about 250% to about 2500% RID. For example, in some embodiments, vitamin B1 is present in an amount of about 1 mg to about 25 mg, of about 10 mg to about 20 mg, of about 10 mg to about 30 mg, of about 5 mg to about 35 mg, or of about 12.5 mg to about 17.5 mg. For example, in some embodiments, vitamin B1 is present in an amount of about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, or about 50 mg.

In some embodiments, vitamin B2 is present in an amount of about 1 mg to about 50 mg, or of about 500% to about 5000% RID. In some embodiments, the vitamin B2 comprises about 90% riboflavin and about 10% riboflavin 5'-monophosphate. For example, in some embodiments, vitamin B2 is present in an amount of about 1 mg to about 25 mg, of about 10 mg to about 20 mg, of about 10 mg to about 30 mg, of about 5 mg to about 35 mg, or of about 12.5 mg to about 17.5 mg. For example, in some embodiments, vitamin B2 is present in an amount of about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, or about 50 mg.

In some embodiments, vitamin B3 is present in an amount of about 1 mg to about 50 mg, or of about 30% to about 300% RID. For example, in some embodiments, vitamin B3 is present in an amount of about 1 mg to about 25 mg, of about 10 mg to about 20 mg, of about 10 mg to about 30 mg, of about 5 mg to about 35 mg, or of about 12.5 mg to about 17.5 mg. For example, in some embodiments, vitamin B3 is present in an amount of about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, or about 50 mg.

In some embodiments, Vitamin B5 is present in an amount of about 5 mg-about 200 mg, or of about 125%-about 1250% RID. For example, in some embodiments, vitamin B5 is present in an amount of about 5 mg to about 150 mg, of about 100 mg to about 200 mg, of about 10 mg to about 100 mg, of about 50 mg to about 100 mg, or of about 125 mg to about 175 mg. In some embodiments, vitamin B5 is present in an amount of about 5 mg, about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, or about 200 mg.

In some embodiments, vitamin B6 is present in an amount of about 1 mg to about 50 mg, or of about 250% to about 2500% RID. In some embodiments, the vitamin B6 comprises about 80% pyridoxine and about 20% pyridoxal 5'-phosphate. In some embodiments, vitamin B6 is present in an amount of about 1 mg to about 25 mg, of about 10 mg to about 20 mg, of about 10 mg to about 30 mg, of about 5 mg to about 35 mg, or of about 12.5 mg to about 17.5 mg. In some embodiments, vitamin B6 is present in an amount of about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, or about 50 mg.

In some embodiments, vitamin B12 is present in an amount of about 25 µg to about 250 µg, or of about 400% to about 4000% RID. In some embodiments, vitamin B12 is present in an amount of about 25 µg to about 200 µg, of about 50 µg to about 150 µg, of about 75 µg to about 125 µg, of about 80 µg to about 120 µg, or of about 85 µg to about 100 µg. In some embodiments, vitamin B12 is present in an amount of about 25 µg, about 30 µg, about 40 µg, about 50 µg, about 60 µg, about 70 µg, about 80 µg, about 90 µg, about 100 µg, about 125 µg, about 150 µg, about 175 µg, about 200 µg, or about 250 µg.

In some embodiments, Vitamin C is present in an amount of about 75 mg-about 750 mg, or of about 125%-about 1250% RID. In certain embodiments, vitamin C is present in an amount of about 100 mg to about 500 mg, of about 200 mg to about 400 mg, of about 250 mg to about 500 mg, of about 500 mg to about 750 mg, or of about 300 mg to about 600 mg. In some embodiments, vitamin C is present in an amount of about 75 mg, about 100 mg, about 150 mg, about 200 mg, about 300 mg, about 400 mg, about 500 mg, about 600 mg, about 700 mg, or about 750 mg.

In some embodiments, vitamin D is present in an amount of about 125 IU to about 1250 IU, or of about 50% to about 500% RID. In certain embodiments, vitamin D is present in an amount of about 150 IU to about 1000 IU, of about 200 IU to about 800 IU, of about 250 IU to about 500 IU, or of about 300 IU to about 500 IU. In some embodiments, vitamin D is present in an amount of about 125 IU, about 150 IU, about 200 IU, about 250 IU, about 500 IU, about 750 IU, about 1000 IU, or about 1250 IU.

In some embodiments, vitamin E is present in an amount of about 20 IU to about 200 IU, or of about 50% to about 500% RID. In certain embodiments, vitamin E is present in an amount of about 25 IU to about 175 IU, of about 50 IU to about 150 IU, of about 60 IU to about 100 IU, or of about 50 IU to about 70 IU. In some embodiments, vitamin E is present in an amount of about 20 IU, about 25 IU, about 50 IU, about 60 IU, about 75 IU, about 100 IU, about 150 IU, about 175 IU, or about 200 IU.

In some embodiments, vitamin K is present in an amount of about 50 µg to about 500 µg, or of about 50% to about 500% RID. In certain embodiments, vitamin K is present in an amount of about 50 µg to about 500 µg, of about 50 µg to about 250 µg, of about 75 µg to about 200 µg, of about 100 µg to about 200 µg, or of about 150 µg to about 200 µg. For example, in some embodiments, vitamin K is present in an amount of about 50 µg, about 100 µg, about 150 µg, about 160 µg, about 175 µg, about 200 µg, or about 250 µg. In some embodiments, the Vitamin K comprises about 97% Vitamin K1 and about 3% Vitamin K2.

In some embodiments, biotin is present in an amount of about 75 µg to about 750 µg, or of about 25% to about 250% RID. In some embodiments, biotin is present in an amount of about 75 µg to about 500 µg, of about 100 µg to about 300 µg, of about 250 µg to about 500 µg, of about 250 µg to about 350 µg, or of about 275 µg to about 325 µg. In some embodiments, Biotin is present in an amount of about 75 µg, about 100 µg, about 200 µg, about 250 µg, about 300 µg, about 350 µg, about 400 µg, about 500 µg, about 600 µg, about 700 µg, or about 750 µg.

In some embodiments, folate is present in an amount of about 100 µg to about 4000 µg, or of about 25% to about 250% RID. In some embodiments, folate is present in an amount of about 100 µg to about 3000 µg, of about 150 µg to about 2500 µg, of about 200 µg to about 500 µg, of about 300 µg to about 500 µg, or of about 250 µg to about 500 µg. In some embodiments, folate is present in an amount of about 100 µg, about 200 µg, about 300 µg, about 400 µg, about 500 µg, about 600 µg, about 700 µg, about 800 µg, about 900 µg, about 1000 µg, about 2000 µg, about 3000 µg, or about 4000 µg.

In some embodiments, PABA is present in an amount of about 7.5 µg to about 75 µg. In some embodiments, PABA is present in an amount of about 7.5 µg to about 50 µg, of about 25 µg to about 50 µg, of about 20 µg to about 40 µg, of about 50 µg to about 75 µg, or of about 30 µg to about 60 µg. In some embodiments, PABA is present in an amount of about 50 µg, about 100 µg, about 150 µg, about 160 µg, about 175 µg, about 200 µg, about 250 µg, about 300 µg, about 400 µg, or about 500 µg.

In some embodiments, boron is present in an amount of about 250 µg to about 2.5 mg. In some embodiments, boron is present in an amount of about 250 µg to about 2000 µg, of about 500 µg to about 1000 µg, of about 750 µg to about 1500 µg, of about 500 µg to about 750 µg, or of about 800 µg to about 1200 µg. In some embodiments, boron is present in an amount of about 250 µg, about 500 µg, about 750 µg, about 1000 µg, about 1250 µg, about 1500 µg, about 2000 µg, or about 2500 µg.

In some embodiments, Chromium is present in an amount of about 50 µg to about 500 µg, or of about 50% to about 500% RID. In some embodiments, chromium is present in an amount of about 50 µg to about 500 µg, of about 50 µg to about 250 µg, of about 75 µg to about 200 µg, of about 100 µg to about 200 µg, or of about 150 µg to about 200 µg. In some embodiments, chromium is present in an amount of about 50 µg, about 100 µg, about 150 µg, about 160 µg, about 175 µg, about 200 µg, about 250 µg, about 300 µg, about 400 µg, or about 500 µg. In some embodiments, the chromium comprises about 50% Chromium picolinate and about 50% chromium ascorbate.

In some embodiments, copper is present in an amount of about 125 µg to about 500 µg, or of about 5% to about 75% RID. In some embodiments, copper is present in an amount of about 125 µg to about 500 µg, of about 150 µg to about 400 µg, of about 200 µg to about 300 µg, of about 100 µg to about 250 µg, or of about 250 µg to about 300 µg. In some embodiments, copper is present in an amount of about 125 µg, about 150 µg, about 200 µg, about 250 µg, about 300 µg, about 350 µg, about 400 µg, about 450 µg, or about 500 µg.

In some embodiments, magnesium is present in an amount of about 40 mg to about 400 mg, or of about 10% to about 100% RID. In some embodiments, magnesium is present in an amount of about 40 mg to about 250 mg, of about 80 mg to about 200 mg, of about 100 mg to about 250 mg, of about 200 mg to about 300 mg, or of about 200 mg to about 250 mg. In some embodiments, magnesium is present in an amount of about 40 mg, about 50 mg, about 60 mg, about 70 mg, about 80 mg, about 90 mg, about 100 mg, about 200 mg, about 300 mg, or about 400 mg. In some embodiments, the magnesium comprises magnesium citrate, magnesium malate, and magnesium succinate.

In some embodiments, manganese is present in an amount of about 1 µg-about 10 µg, or of about 50%-about 750% RID.

In some embodiments, manganese is present in an amount of about 1 µg to about 5 µg, of about 2.5 µg to about 7.5 µg, of about 5 µg to about 10 µg, of about 4 µg to about 6 µg, or of about 1 µg to about 2.5 µg. For example, in some embodiments, manganese is present in an amount of about 1 µg, about 2 µg, about 3 µg, about 4 µg, about 5 µg, about 6 µg, about 7 µg, about 8 µg, about 9 µg, or about 10 µg.

In some embodiments, molybdenum is present in an amount of about 25 µg-about 250 µg, or of about 30%-about 500% RID. In some embodiments, molybdenum is present in an amount of about 25 µg to about 50 µg, of about 100 µg to about 200 µg, of about 100 µg to about 150 µg, of about 50 µg to about 100 µg, or of about 75 µg to about 150 µg. In some embodiments, molybdenum is present in an amount of about 25 µg, about 50 µg, about 75 µg, about 100 µg, about 125 µg, about 150 µg, about 200 µg, about 225 µg, or about 250 µg.

In some embodiments, selenium is present in an amount of about 30 µg to about 300 µg, or of about 40% to about 400% RID. In some embodiments, selenium is present in an amount of about 30 µg to about 250 µg, of about 30 µg to about 100 µg, of about 50 µg to about 150 µg, of about 100 µg to about 200 µg, or of about 150 µg to about 250 µg. In some embodiments, selenium is present in an amount of about 30 µg, about 40 µg, about 50 µg, about 60 µg, about 70 µg, about 80 µg, about 90 µg, about 100 µg, about 200 µg, about 250 µg, or about 300 µg.

In some embodiments, vanadium is present in an amount of about 25 µg to about 250 µg. In some embodiments, vanadium is present in an amount of about 25 µg to about 50 µg, of about 100 µg to about 200 µg, of about 100 µg to about 150 µg, of about 50 µg to about 100 µg, or of about 75 µg to about 150 µg. In some embodiments, vanadium is present in an amount of about 25 µg, about 50 µg, about 75 µg, about 100 µg, about 125 µg, about 150 µg, about 200 µg, about 225 µg, or about 250 µg.

In some embodiments, zinc is present in an amount of about 5 mg to about 50 mg, or of about 30% to about 300% RID.

In some embodiments, iodine is present in an amount of about 40 µg to about 400 µg, or of about 25% to about 250% RID. In some embodiments, iodine is present in an amount of about 40 µg to about 250 µg, of about 80 µg to about 200 µg, of about 100 µg to about 250 µg, of about 200 µg to about 300 µg, or of about 200 µg to about 250 µg. In some embodiments, Iodine is present in an amount of about 40 µg, about 50 µg, about 60 µg, about 70 µg, about 80 µg, about 90 µg, about 100 µg, about 200 µg, about 300 µg, or about 400 µg.

In some embodiments, bromelain is present in an amount of about 50 mg to 750 mg. In some embodiments, bromelain is present in an amount of about 50 mg to about 500 mg, of about 50 mg to about 250 mg, of about 75 mg to about 200 mg, of about 100 mg to about 200 mg, or of about 150 mg to about 200 mg. In some embodiments, bromelain is present in an amount of about 50 mg, about 100 mg, about 150 mg, about 200 mg, about 250 mg, about 500 mg, or about 750 mg.

In some embodiments, a flavonoid is present in an amount of about 50 mg to 750 mg. In some embodiments, quercetin is present in an amount of about 50 mg to 750 mg. In some embodiments, a flavonoid is present in an amount of about 50 mg to about 500 mg, of about 50 mg to about 250 mg, of about 75 mg to about 200 mg, of about 100 mg to about 200 mg, or of about 150 mg to about 200 mg. In some embodiments, a flavonoid is present in an amount of about 50 mg, about 100 mg, about 150 mg, about 200 mg, about 250 mg, about 500 mg, or about 750 mg.

In some embodiments, pomegranate extract is present in an amount of about 0.3 mg to about 3 mg. In some embodiments, pomegranate extract is present in an amount of about 0.3 mg to about 2 mg, of about 0.5 mg to about 1 mg, of about 1 mg to about 2.5 mg, of about 1.5 mg to about 2 mg, or of about 0.5 mg to about 2 mg. In some embodiments, pomegranate extract is present in an amount of about 0.3 mg, about 0.4 mg, about 0.5 mg, about 0.6 mg, about 0.7 mg, about 0.8 mg, about 0.9 mg, about 1 mg, about 1.5 mg, about 2 mg, about 02.5 mg, or about 3 mg.

The compositions provided herein may comprise any combination or sub-combination of the foregoing components.

For example, a typical composition for recovery from surgery or an athletic performance as provided by some embodiments described herein comprises about 15 mg of vitamin B1, about 34 mg of vitamin B2, about 25 mg of vitamin B3, about 50 mg of vitamin B5, about 20 mg of vitamin B6, about 90 µg of vitamin B12, about 60 IU of vitamin E, about 1 mg of boron, about 250 mg of bromelain, and about 250 mg of quercetin.

Another exemplary typical serving of a composition for recovery from surgery or athletic performance as provided by some embodiments described herein comprises about 5000 IU of Vitamin A, about 15 mg of Vitamin B1, about 34 mg of Vitamin B2, about 25 mg of Vitamin B3, about 50 mg of Vitamin B5, about 20 mg of Vitamin B6, about 90 µg of Vitamin B12, about 300 mg of Vitamin C, about 500 IU of Vitamin D, about 60 IU of Vitamin E, about 160 µg of Vitamin K1, about 5 µg of Vitamin K2, about 300 µg of Biotin, about 400 µg of Folate, about 30 µg of PABA, about 1 mg of Boron, about 200 µg of Chromium, about 500 µg of Copper, about 150 mg of Magnesium, about 5 µg of Manganese, about 100 µg of Molybdenum, about 135 µg of Selenium, about 100 µg of Vanadium, about 20 mg of Zinc, about 150 µg of Iodine, about 1.2 mg of pomegranate extract, about 250 mg of Bromelain, and about 250 mg of Quercetin.

Some aspects of this disclosure provide a dosage form comprising a composition described herein. A dosage form may be a formulation of a composition provided herein in a form that can be administered to a subject. While parenteral administration routes are suitable for administering some of the compositions provided herein to a subject, enteral routes, and in particular oral administration routes, are preferred. Accordingly, in some embodiments, the dosage form is formulated for oral administration, for example, in the form of a pill, a tablet, a beverage, a syrup, an elixir, a tincture, or an effervescent formulation, e.g., for the preparation of a beverage. Typically, a dosage form comprises the active ingredients, e.g., vitamins, minerals, and co-factors, and a pharmaceutically acceptable carrier or excipient. In some embodiments, the carrier comprises a comprises a vegetable fiber matrix, stearic acid, croscarmellose sodium, modified cellulose, dicalcium phosphate, hydroxypropyl methylcellulose, magnesium stearate, silicon dioxide, brown rice, and/or water.

In some embodiments, a composition provided herein is specifically formulated to exclude various ingredients that are known in the art to be allergens. Exemplary ingredients, food products, or derivatives therefrom, that are specifically excluded from some compositions provided herein are: casein or milk derivatives, corn, fish, shellfish, gluten, monosodium glutamate (MSG), nuts, processed sugar, soy, and wheat.

Any of the compositions provided herein may further include one or more suitable additive. Suitable additives for compositions for administration to a subject are known to those of skill in the art and include, without limitation, flavors, sweeteners, colors, binders, diluents, fillers, compaction agents, effervescent agents, non-effervescent disintegrants, excipients, and solvents.

In embodiments providing a composition for oral administration, a suitable flavor for use in the formulation of a dosage form may be chosen from synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds, and cassia oil. Also useful as flavors are vanilla, citrus oil, including lemon, orange, grape, lime and grapefruit, and fruit essences, including apple, pear, peach, strawberry, raspberry, cherry, plum, pineapple, apricot, and so forth. Flavors, which have been found to be particularly useful, include commercially available orange, grape, cherry, and bubble gum flavors, and mixtures thereof. The amount of flavoring may depend on a number of factors, including the organoleptic effect desired. Flavors may be present in an amount ranging from about 0.5% to about 3.0% by weight of the composition. Commonly accepted flavors include grape and cherry flavors, and citrus flavors such as orange, lemon, and lime. It is also appreciated that inclusion of flavoring agents can influence the final flavor of the vehicle, furthering compliance with ingestion of the dietary supplement.

The composition may also comprise a sweetener. Suitable sweeteners for use in the composition of the invention include, but are not limited to, carbohydrates, mono-saccharides, di-saccharides, polysaccharides of simple sugars, and sugar derivatives. Exemplary sweeteners include, but are not limited to, high caloric sugars such as sucrose, lactose, glucose, d-glucose, l-glucose, maltose, dextrose, fructose, fructosan, gentiobiose, cellobiose, panose, malto-triose, malto-tetrose, arabinose, mannose, d-mannose, galactose, d-galactose, d-glyceraldehyde, amylose, allose, altose, talose, gulose, idose, ribose, erythrose, threose, lyxose, xylose, d-xylose, rhamnose, invert sugar, inositol, glycerol, glycogen, pectin, agar, sorbitol, mannitol and combinations thereof; low caloric sugars, such as sucralose, polyols, tagarose, trehalose, xylitol, dextrans, dextrins, dextrates, polysorbates, maltodextrin, xylitol, amylase, amylopectin, ribose, .beta.-maltose, fucose, sialic acid (neuraminic acid), N-acetylgalactosamine, N-acetylglucosamine, sedoheptulose, ribulose, xylulose and combinations thereof; non-sugar sweeteners, such as acesulfame potassium, aspartame, neotame, saccharin, stevioside and combinations thereof.

In some embodiments, a composition as provided herein may comprise a coloring agent. Suitable coloring agents include, without limitation, titanium dioxide, and dyes suitable for food such as those known as F.D.&C. dyes and natural coloring agents such as grape skin extract, beet red powder, beta-carotene, annato, carmine, turmeric, paprika, etc. The amount of coloring used may range from about 0.1% to about 3.5% by weight of the final composition.

Examples of binders which can be used in the compositions and dosage forms provided herein include acacia, tragacanth, gelatin, starch, cellulose materials such as methyl cellulose and sodium carboxy methyl cellulose, alginic acids and salts thereof, magnesium aluminum silicate, polyethylene glycol, guar gum, polysaccharide acids, bentonites, sugars, invert sugars and the like. Binders may be used in an amount up to about 60% by weight and advantageously from about 10% to about 40% by weight of the total composition.

Some compositions and dosage forms provided herein contain a disintegrant. Exemplary disintegrants that may be used in the compositions and dosage forms provided herein include, but are not limited to, starches, e.g., potato starch and modified starches thereof, sweeteners, clays, such as bentonite, micro-crystalline cellulose, alginates, gums such as agar, guar, locust bean, karaya, pectin and tragacanth. Disintegrants may comprise up to about 20% by weight and advantageously between about 2% and about 10% by weight of the final composition. Notably, these binders and disintegrants may already be sufficiently present in other components of the formulation.

In some embodiments, the individual components of a composition or dosage form provided herein are formulated into a solid composition for oral administration to a subject. Suitable solid compositions include, without limitation, orally dispersible pills, chewable pills, buccal adhesive pills, tablets, capsules including hard or soft-shelled gelatin capsules, granular powder, troches, and dragees. These formulations may be prepared by techniques known in the art. For example, a pill may be manufactured by well-known pill manufacturing procedures.

Known granulation and wet-granulation methods for forming tablets may be utilized. Granulation generally includes any process of size enlargement whereby small particles are gathered together into larger, permanent aggregates to yield a free-flowing composition having a consistency suitable for tableting. Such granulated compositions may have consistency similar to that of dry sand. Granulation may be accomplished by agitation in mixing equipment or by compaction, extrusion or globulation. Granulation also includes, for example, a process where a liquid form of a material is rendered granular, or in a solid form, by combining it with a granular core material, such as a sugar particle. Such granular material may be produced, for example, by spray-drying the liquid onto the core particle. Thus, individual materials may be granulated to lend themselves to tableting.

In some embodiments, a lubricant may be used in the manufacture of tablets. Without the use of an effective lubricant, tableting by use of high-speed equipment may be difficult. As used herein, the term "lubricant" refers to a material that can reduce the friction arising at the interface of the tablet and the die wall during compression and ejection thereof. Lubricants may also serve to prevent sticking to the punch and, to a lesser extent, the die wall as well. Extrinsic or intrinsic lubricants may be incorporated in the material to be tableted. A lubricant that is directly applied to the tableting tool surface in the form of a film, as by spraying onto the die cavity and/or punch surfaces, is known as an extrinsic lubricant. Although extrinsic lubricants can provide effective lubrication, their use requires complex application equipment and methods which add cost and reduce productivity. Magnesium, calcium and zinc salts of stearic acid have long been regarded as the most efficient intrinsic lubricants in common use. Concentrations of 1% or less by weight are usually effective. Other traditional intrinsic lubricants include hydrogenated and partially hydrogenated vegetable oils, animal fats, polyethylene glycol, polyoxyethylene monostearate, talc, light mineral oils, sodium benzoate, sodium lauryl sulphate, magnesium oxide and the like. See Leal, et al., U.S. Pat. No. 3,042,531, the disclosure of which is incorporated herein by reference in its entirety.

In another aspect, the compositions and dosage forms provided herein may be formulated into a solid composition for placement in an aqueous vehicle for oral administration. In some such embodiments, it is contemplated that the formulation would further include an effervescing agent for dispersing the components of the formulation within the aqueous vehicle. As used herein, the term aqueous vehicle refers to a medium or a carrier, such as a foodstuff containing at least a minimal amount of water. Thus, the aqueous vehicle may be an oligohydrous vehicle containing a small amount of water, or it may be a vehicle having an abundance of water contained therein, e.g., a beverage, such as water or juice.

The term foodstuff, as used herein, is intended to refer to any safe, consumable liquid, semi-solid, or solid substance. Thus, a foodstuff would include any beverage and any food, which may be consumed by mammals of all classes and ages. As used herein, the term "effervescence" generally means the escape of a gas from a liquid or mixture (Hawley's Chemical Dictionary, pp. 432, 2001). Thus, the term "effervescent agent," is intended to generally refer to a composition or mixture of components that evolve one or more gases, under proper conditions, such as upon contact with water.

In some embodiments, the effervescing agent is a mixture of compounds that evolve gas. These compounds should be capable of reacting upon exposure of one or both of the reactants to water, such as the water contained in aqueous fluids or other aqueous vehicles, to produce and/or evolve the gas. In some embodiments, the effervescing mixture includes at least one acidic component and at least one basic component. In this instance, the acidic and basic components react, upon exposure to water, with one another to produce at least one gas. For example, the reaction between a soluble acid, or source thereof, with an carbonate, or source thereof such as an alkaline metal carbonate, generally evolves $CO_2$ gas. More particularly, when such a gas-generating effervescent mixture is placed in a minimal amount of water, or water-containing vehicle such as saliva, $CO_2$ gas is generally produced and bubbles out of the water or aqueous vehicle.

The acidic component may be an acid or source thereof and should be safe for consumption. Suitable acids include, but are not limited to, food acids, acid anhydrides and acid salts. Exemplary food acids include, but are not limited to, citric acid, tartaric acid, malic acid, fumaric acid, adipic acid, and succinic acid. Anhydrides of the above-described acids may also be used because anhydrides generally degrade in the presence of water to generate the reactive acid. Exemplary suitable acid salts include, but are not limited to, sodium dihydrogen phosphate, disodium dihydrogen pyrophosphate, acid citrate salts and sodium acid sulfite. Acid salts generally disassociate in water, or in the water content of the aqueous vehicle, to provide the reactive acid species. The overall solubility of the acid, or source thereof, in water will vary and is appreciated by those of skill in the art. The effectiveness of the acid in generating the gas, and the amount of gas generated, is generally dependent on water solubility of the acid form in the dietary supplement.

Similarly, the basic component may be a carbonate or source thereof and should be safe for consumption. Suitable carbonate sources include, but are not limited to, dry solid carbonate, bicarbonate, sesquicarbonate, and sesquibicarbonate salts of metals, such as sodium, potassium, lithium, calcium, and magnesium. Examples of suitable carbonates include, without limitation, sodium carbonate, sodium bicarbonate, sodium sesquicarbonate, potassium carbonate, potassium bicarbonate, potassium sesquicarbonate, magnesium carbonate, sodium glycine carbonate, L-lysine carbonate, arginine carbonate, and amorphous calcium carbonate. Ammonium carbonate and ammonium bicarbonate are also suitable carbonates. In addition, any combination of the above sources of carbonate may be used as the basic component in the effervescing mixture.

It should be understood that the gas-generating effervescent component(s) are not limited to components reactive to form only carbon dioxide gas. Pharmaceutically safe reactants that evolve oxygen, nitrogen, helium, ethylene oxide, or other inert gases are also considered within the scope of the invention. For example, peroxides such as hydrogen peroxide, sodium peroxide and the like are capable of releasing useful oxygen gas. The combination of horse-radish with hydrogen peroxidase for example, or a vegetable peroxidase, is known to evolve oxygen gas. In addition, the gas-generating effervescent component(s) are not limited to mutually reactive components, such as the acidic and basic components described above, but may include safe, compounds, reactive with water to release a gas. Use of safe gas-generating effervescent component(s) and gases generated therefrom is particularly important in dietary supplements designed for oral administration.

The effectiveness of the effervescing agent to disperse the vitamins, minerals, and antioxidants of the dietary supplement is generally related to the degree of "pop" caused by the abrupt release of gas. As disclosed in U.S. Pat. No. 4,837,039, the disclosure of which is incorporated herein by reference in its entirety, the quantity and intensity of each "pop" is generally dependent upon the size of the bubble, the pressure of the gas contained in the bubble, the surface tension of the bubble, and the degree of solubility of the ingredients of the solid matrices in water or an aqueous vehicle. For example, the intensity of the release of gas depends upon the relation of the pressure of the occluded gas to resistance of the film of the bubble and on the diameter of the bubble trapping the gas.

In some embodiments, the dietary supplements of the invention may be formulated to optimize exposure of the effervescing agent to the water content of the aqueous vehicle. For example, the formulation may contain a plurality of layers including an outermost layer and a core. Any of the components, including the effervescing agents, vitamins, minerals, and co-factors, may be included in the outermost layer or distributed as desired between the outermost layer and the core. Thus, bi-layered or multi-layered tablet or pill formulations are contemplated herein.

In some embodiments, the dietary supplement is varied in shape. For example, while conventional oval shapes of a tablet or round shapes of a pill exist, the formulation may be provided in a non-traditional shape so as to increase the surface area of the formulation that is exposed to the vehicle. Particularly, for oligohydrous vehicles having minimal water content, exposing a maximum surface area of the formulation will enhance the rate of effervescence, thereby promoting the rate of distribution of the vitamins, minerals, and antioxidants into the vehicle. Generally, human subjects do not prefer to wait for a lengthy period of time before ingesting the vehicle. Therefore, in some embodiments, the solid formulation, such as a tablet or pill, has a biconcave shape to increase the surface area for contact with the vehicle. Such a shape may also comprise multiple layers, as previously discussed herein, wherein one or more layers contain one or more of the components of the dietary supplement. Optimal exposure of these components generally minimizes the time required to disperse the vitamins, minerals, and antioxidants into the vehicle by the effervescence of gas.

Formulations containing an effervescing agent may be orally administered to the subject in need of dietary supplementation in a variety of ways. For example, the tablet(s) is initially placed in an aqueous vehicle, where it may be further stirred and/or agitated to commence effervescence of gases within the vehicle. Vehicles containing as little as about 0.1 ml of total water content are generally suitable to commence effervescence of gas(es) from the formulation. The effervescing gases promote penetration and distribution of the vitamins, minerals, and antioxidants into the vehicle. In some embodiments, the dietary supplement formulation is placed into a vehicle containing up to about 5 ml of water. In another embodiment, the dietary supplement formulation is placed into a vehicle containing up to about 6 ounces of water. In another embodiment, the effervescent formulation is placed in a vehicle containing between about 5 ml and about 15 ml of water. In yet another embodiment, the effervescent formulation is placed in a vehicle containing at least about 15 ml of water.

In some aspect, the invention provides a method for enhancing the recovery of a subject from surgery or from athletic performance. The methods provided herein generally include administering a therapeutically effective amount of a composition provided herein to a subject in temporal proximity to a surgery or to athletic performance. The term temporal proximity refers to a coincidence of the surgery or the athletic performance, and the commencement of administration of a composition or dosage form provided herein within a relatively short period of time. For example, administering a composition provided herein in temporal proximity to a surgery or athletic performance may involve administering the composition within hours (e.g., about 1 hour, about 2 hours, about 3 hours, about 4 hours, about 5 hours, about 6 hours, about 8 hours, about 10 hour, about 12 hours, about 18 hours, about 24 hours, about 30 hours, about 36 hours, about 42 hours, or about 48 hours) or within days (e.g., about 1 day, about 2 days, about 3 days, about 4 days, about 5 days, about 6, or about 7 days) before or after the surgery or an athletic performance, or at about the same time as the surgery or athletic performance.

In some embodiments, a composition described herein is administered to a subject after the subject has undergone a surgery to support recovery. In some embodiments, a daily dose of a composition as described in U.S. Patent Application Publication Number US 2011/0293759 is administered to a subject prior to the subject undergoing surgery, e.g., for about 1-2 weeks prior to surgery, and a composition as described herein is administered to the subject, e.g., in the form of daily dosages starting on the day of surgery or the day after surgery, and for a time period of 1 week to 1 year (e.g., for a time period of about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, or about 52 weeks.

The term subject as used herein refers to an individual. In some embodiments, the subject is human of either sex and at any stage of development. In some embodiments, the subject is an animal, e.g., a mammal, such as a rodent (including, e.g., a mouse, rat, hamster, and guinea pig), a cat, a dog, a rabbit, a farm animal (including, e.g., a cow, a horse, a goat, a sheep, a pig), or a primate (including, e.g., non-human primates).

In some embodiments, a composition or dosage form is administered to a subject undergoing surgery peri-operatively or post-operatively to aid in recovery from the surgery. In some embodiments, the surgery is cardiac surgery, urology surgery, gynecologic surgery, ocular surgery, plastic surgery, bariatric surgery, brain surgery, shoulder surgery, elbow surgery, hand surgery, hip surgery, knee surgery, ankle surgery, spine surgery, or fracture surgery.

In some embodiments, the compositions provided herein are combined with other vitamins/minerals/co-factors to provide targeted supplement combinations specific for a wide array of surgeries. For example, in some embodiments, e.g., in embodiments where the composition or dosage form provided does not comprise calcium, a calcium supplement may be given to the subject concurrently with the instantly provided composition or dosage form, e.g., in the form of a separate calcium citrate tablet.

In embodiments, where a composition or dosage form is administered to a subject in a clinical context, the amount administered is typically a therapeutically effective amount. As used herein, the term therapeutically effective amount or effective amount refers to the amount of a composition or dosage form that will elicit a desired biological or clinical response of a tissue, system, or subject, e.g., an enhanced recovery from surgery or athletic performance.

While some of the compositions and dosage forms provided herein may be formulated for oral administration, it will be understood that the compositions and dosage forms described herein may be formulated to be administered to a subject by any suitable route or mode. Exemplary suitable modes of administration include, but are not limited to, intravenously, intra-arterially, subcutaneously, intraperitoneally, intramuscularly, or orally.

The total amount of a composition or dosage form to be administered to a subject may be administered as a single dose or using a fractionated treatment protocol, in which multiple doses are administered over a prolonged period of time (e.g., once daily, twice daily, etc.). When administered orally in pill or tablet form, a dose or serving size of the dietary supplements of the invention may be administered as a single tablet or fractionated into multiple (e.g., 2, 3, 4, 5, 6, or more) tablets. In some embodiments, the dietary supplement is administered to the subject daily. In some embodiments, the dietary supplement is administered to the subject once per day, twice per day, three times per day, four times per day, or more often. In some embodiments, the dietary supplement is administered to the subject once per day, twice per day, three times per day, four times per day, or more often, for a period of 1 day, 2 days, 3 days, 4 days, 5 days, 6 days, 1 week, 10 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, or about 52 weeks.

In certain embodiments, the dietary supplements of the invention may further be administered in combination with other therapeutic agents or compositions, for example, in combination with an antiinflammatory, antimicrobial, antihistamine, chemotherapeutic agent, antiangiogenic agent, therapeutic antibody, a protein kinase inhibitor, e.g., a tyrosine kinase inhibitor, a cytokine, an immunomodulatory agent, an antiviral agent, an antibiotic, an anti-fungal agent, or an anti-parasitic agent. When other therapeutic agents are contemplated for use in combination with a composition or dosage form provided herein, they may be used for example in amounts as noted in the Physician Desk Reference (PDR) or as otherwise determined by one having ordinary skill in the art.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

A composition for oral administration was formulated according to the list of Table 2, such that a full dose/serving was contained in two tablets. Each tablet, accordingly, contained 50% of the components and amounts listed in Table 2. The tablets are administered to a subject at a dosage of one tablet twice daily. As such, the subject consumes one serving of the nutrients listed in Table 2 per day. Where the composition is administered to a subject for recovery after surgery, administration is commenced on the day of surgery or the day after surgery, and continued for at least two weeks, and up to one year or longer, until the subject has recovered. Where the composition is administered to a subject for recovery from athletic performance, administration is commenced on the day of athletic performance and continued for at least one day, and up to one week or longer, until the subject has recovered. The composition was formulated to exclude casein or milk derivatives, corn, fish or shellfish, gluten, MSG, nuts, processed sugar, soy, and wheat.

TABLE 2

Dietary supplement composition.

| | Amount per serving | % Daily Value |
|---|---|---|
| Vitamins | | |
| Vitamin A (beta carotene) 15% (750 IU) Retinyl Acetate/85% (4250 IU) Beta-carotene | 5000 IU | 100% |
| Vitamin B1 (thiamine HCl) | 15 mg | 1000% |
| Vitamin B2 riboflavin 45 mg/ riboflavin 5'-monophosphate 5 mg | 34 mg | 2000% |
| Vitamin B3 (niacin) | 25 mg | 125% |
| Vitamin B5 (calcium d-pantothenate) | 50 mg | 500% |
| Vitamin B6 pyridoxine HCL 80 mg/ pyridoxal 5'-phosphate 20 mg | 20 mg | 1000% |
| Vitamin B12 (hydroxycobalamin acetate) | 90 mcg | 1500% |
| Vitamin C (l-ascorbate) | 300 mg | 500% |
| Vitamin D-3 (cholecalciferol) | 500 IU | 125% |
| Vitamin E (as mixed tocopherols) | 60 IU | 200% |
| Vitamin K-1 (phylloquinone) | 160 µg | 200% |
| Vitamin K2 (menatetranone, MK-4) | 5 µg | * |
| Biotin (crystalline - scientifically pure) | 300 µg | 100% |
| Folate (folic acid) | 400 µg | 100% |
| PABA (para-aminobenzoic acid) | 30 µg | * |
| Minerals | | |
| Boron (ascorbate) | 1 mg | * |
| Chromium (picoinate 100 mcg/ascorbate 100 mcg) | 200 µg | 167% |
| Copper (copper citrate) | 500 µg | 25% |
| Magnesium (as citrate, malate, succinate) | 150 mg | 38% |
| Manganese (ascorbate) | 5 µg | 248% |
| Molybdenum (ascorbate) | 100 µg | 133% |
| Selenium (l-selenomethianone) | 135 µg | 150% |
| Vanadium (ascorbate) | 100 µg | * |
| Zinc (picolinate) | 20 mg | 133% |
| Iodine | 150 µg | 100% |

TABLE 2-continued

Dietary supplement composition.

| | Amount per serving | % Daily Value |
|---|---|---|
| Co-factors | | |
| Vegetable fiber matrix | | |
| Pomegranate extract (antioxidant) | 1.2 mg | * |
| Bromelain | 250 mg | * |
| Quercetin | 250 mg | * |

* = N/A

REFERENCES

1. Semba R D. The role of vitamin A and related retinoids in immune function. Nutr Rev. 1998; 56(1 Pt 2):S38-48.
2. Ross A C. Vitamin A and retinoids. In: Shils M, ed. Nutrition in Health and Disease. 9th ed. Baltimore: Williams & Wilkins; 1999:305-327.
3. Weimann B I, Hermann D. Studies on wound healing: effects of calcium D-pantothenate on the migration, proliferation and protein synthesis of human dermal fibroblasts in culture. Int J Vitam Nutr Res. 1999; 69(2):113-119.
4. Lacroix B, Didier E, Grenier J F. Role of pantothenic and ascorbic acid in wound healing processes: in vitro study on fibroblasts. Int J Vitam Nutr Res. 1988; 58(4):407-13.
5. Aprahamian M, Dentinger A, Stock-Damgé C, Kouassi J C, Grenier J F. Effects of supplemental pantothenic acid on wound healing. Am J Clin Nutr. 1985 March; 41(3):578-89. PubMed PMID: 3976557.
6. Scholl D, Langkamp-Henken B. Nutrient recommendations for wound healing. J Intraven Nurs. 2001 March-April; 24(2):124-32. Review. PubMed PMID: 11836837.
7. Fu L, Tang T, Miao Y, Hao Y, Dai K. Effect of 1,25-dihydroxy vitamin D3 on fracture healing and bone remodeling in ovariectomized rat femora. Bone. 2009 May; 44(5):893-8. Epub 2009 Feb. 5.
8. Segaert S. Vitamin D regulation of cathelicidin in the skin: toward a renaissance of vitamin D in dermatology? J Invest Dermatol. 2008 April; 128(4):773-5.
9. van Etten E, Gysemans C, Branisteanu D D, Verstuyf A, Bouillon R, Overbergh L, Mathieu C. Novel insights in the immune function of the vitamin D system: synergism with interferon-beta. J Steroid Biochem Mol. Biol. 2007 March; 103(3-5):546-51. Epub 2006 Dec. 23.
10. Shearer M J. Vitamin K metabolism and nutriture. Blood Rev. 1992 June; 6(2):92-104.
11. Ishida Y. [Vitamin K2]. Clin Calcium. 2008 October; 18(10):1476-82.
12. Brody T. Nutritional Biochemistry. 2nd ed. San Diego: Academic Press; 1999.
13. Uauy R, Olivares M, Gonzalez M. Essentiality of copper in humans. Am J Clin Nutr. 1998; 67(5 Suppl):9525-9595.
14. Johnson M A, Fischer J G, Kays S E. Is copper an antioxidant nutrient? Crit. Rev Food Sci Nutr. 1992; 32(1):1-31.
15. O'Dell B L. Role of zinc in plasma membrane function. J. Nutr. 2000; 130(5S Suppl):1432S-1436S.
16. Jurenka J S. Therapeutic applications of pomegranate (*Punica granatum* L.): a review. Ahern Med. Rev. 2008 June; 13(2):128-44.
17. Traber M G. Vitamin E and K interactions—a 50-year-old problem. Nutr Rev. 2008 November; 66(11):624-9.

All publications, patents, patent applications, publication, and database entries mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the invention encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A composition comprising
(a) pyridoxal;
(b) vitamin E;
(c) boron;
(d) a protease; and
(e) a flavonoid.

2. The composition of claim 1, wherein the composition further comprises a B vitamin selected from the group consisting of vitamin B1, vitamin B2, vitamin B3, vitamin B5, pyridoxine, vitamin B12, and combinations thereof.

3. The composition of claim 2, wherein the Vitamin B5 is pantothenic acid and/or pantothenate.

4. The composition of claim 1, wherein the composition further comprises a vitamin selected from the group consisting of vitamin A, vitamin C, vitamin D, vitamin K, biotin, folic acid, folate, para-aminobenzoic acid (PABA), and salts thereof.

5. The composition of claim 4, wherein the vitamin D is vitamin D3.

6. The composition of claim 4, wherein the vitamin K is vitamin K1 and/or vitamin K2.

7. The composition of claim 4, wherein the Vitamin A is beta carotene, retinol, and/or retinoic acid; the Vitamin C is ascorbic acid and/or ascorbate; the Vitamin D is cholecalciferol; the Vitamin E is tocopherol; and/or the Vitamin K is phylloquinone and/or menatetranone.

8. The composition of claim 1 further comprising a mineral selected from the group consisting of chromium, copper, magnesium, manganese, molybdenum, selenium, vanadium, zinc, iodine, and calcium.

9. The composition of claim 8, wherein at least one mineral is provided as a salt selected from the group consisting of acetate, ascorbate, citrate, malate, succinate, picolinate, methionine, and methianone.

10. The composition of claim 1, wherein the protease is a plant protease.

11. The composition of claim 1, wherein the protease comprises bromelain.

12. The composition of claim 1, wherein the composition further comprises an antioxidant.

13. The composition of claim 12, wherein the antioxidant comprises a plant extract.

14. The composition of claim 13, wherein the antioxidant comprises pomegranate extract.

15. The composition of claim 1, wherein the composition further comprises calcium.

16. The composition of claim 1, wherein the pyridoxal, the vitamin E, the boron, the protease, and the flavonoid are present in therapeutically effective amounts.

17. A composition comprising vitamin A, vitamin B1, vitamin B2, vitamin B3, vitamin B5, vitamin B6, vitamin B12, vitamin C, vitamin D, vitamin E, vitamin K, biotin, folate, PABA, boron, chromium, copper, magnesium, manganese, molybdenum, selenium, vanadium, zinc, iodine, bromelain, and a flavonoid.

18. The composition of claim 17, wherein the flavonoid comprises quercetin.

19. A composition comprising about 5000 IU of vitamin A, about 15 mg of vitamin B1, about 34 mg of vitamin B2, about 25 mg of vitamin B3, about 50 mg of vitamin B5, about 20 mg of vitamin B6, about 90 µg of vitamin B12, about 300 mg of vitamin C, about 500 IU of vitamin D, about 60 IU of vitamin E, about 160 µg of vitamin K1, about 5 µg of vitamin K2, about 300 µg of biotin, about 400 µg of folate, about 30 µg of PABA, about 1 mg of boron, about 200 µg of chromium, about 500 µg of copper, about 150 mg of magnesium, about 5 µg of manganese, about 100 µg of molybdenum, about 135 µg of selenium, about 100 µg of vanadium, about 20 mg of zinc, about 150 µg of iodine, about 1.2 mg of pomegranate extract, about 250 mg of bromelain, and about 250 mg of quercetin.

* * * * *